United States Patent
Jonas et al.

(10) Patent No.: US 7,128,901 B2
(45) Date of Patent: Oct. 31, 2006

(54) EXTRUDED STICK PRODUCT AND METHOD FOR MAKING SAME

(75) Inventors: John Jonas, Summit, NJ (US); Steven Misner, Verona, NJ (US)

(73) Assignee: Colgate-Palmolive Company, New York, NY (US)

(*) Notice: Subject to any disclaimer, the term of this patent is extended or adjusted under 35 U.S.C. 154(b) by 524 days.

(21) Appl. No.: 10/454,018

(22) Filed: Jun. 4, 2003

(65) Prior Publication Data

US 2004/0247545 A1   Dec. 9, 2004

(51) Int. Cl.
*A61Q 15/00* (2006.01)
(52) U.S. Cl. .................. 424/65; 424/66; 424/67; 424/68; 424/400; 424/401
(58) Field of Classification Search .......... 424/65, 424/66, 67, 68, 400, 401
See application file for complete search history.

(56) References Cited

U.S. PATENT DOCUMENTS

| 4,278,658 A * | 7/1981 | Hooper et al. ............ 424/65 |
| 4,688,609 A | 8/1987 | Diaz |
| 4,897,236 A | 1/1990 | Rabiger et al. |
| 5,316,712 A | 5/1994 | Ono et al. |
| 5,490,979 A | 2/1996 | Kasat et al. |
| 6,045,814 A | 4/2000 | Roulier et al. |
| 6,161,579 A | 12/2000 | Vulliet |
| 6,261,579 B1 | 7/2001 | Roulier et al. |
| 6,338,840 B1 | 1/2002 | Allan et al. |
| 6,703,005 B1 * | 3/2004 | Allan et al. ............ 424/65 |
| 2001/0041169 A1 | 11/2001 | Allan et al. |
| 2002/0085983 A1 | 7/2002 | Fleissman et al. |
| 2003/0152539 A1 | 8/2003 | Scavone |

FOREIGN PATENT DOCUMENTS

| EP | 0512 770 A1 | 11/1992 |
| FR | 2 194 113 | 2/1974 |
| WO | WO 92/19221 | 11/1992 |
| WO | WO 99/07429 | 2/1999 |
| WO | WO 00/19861 | 4/2000 |
| WO | WO 00/41169 | 7/2000 |
| WO | WO 01/02824 | 1/2001 |
| WO | WO 01/76409 | 10/2001 |
| WO | WO 02/053109 | 12/2001 |

* cited by examiner

*Primary Examiner*—Shelley A. Dodson
(74) *Attorney, Agent, or Firm*—Michael F. Morgan

(57) ABSTRACT

A process for forming a free standing antiperspirant or deodorant solid stick product using particulate and fluid materials that are combined by means of amalgamation, homogenization, compaction and extrusion at a temperature below the melting temperature of said product and extruded by mechanically working the particulate and fluid materials.

6 Claims, 1 Drawing Sheet

EXTRUDED STICK PRODUCT AND METHOD FOR MAKING SAME

FIELD OF THE INVENTION

This invention relates to a new extrusion method and an improved stick product resulting therefrom for making a cosmetic product such as an antiperspirant and/or deodorant product, sunscreens, or bug repellants at lower temperatures than traditionally used. The product may be formed without requiring a package thereby having environmental advantages.

BACKGROUND OF THE INVENTION

Traditional methods of manufacturing antiperspirant and/or deodorant sticks utilize hot processes that form a melt, or near molten fluid, which is poured or forced into a container and then cooled to form a solid stick.

In the underarm area, art of interest includes U.S. Patent Application No. 2001/0041169 A1 to Allan et al for Unilever, published Nov. 15, 2001, which describes a filling process for containers wherein the product is close to the setting temperature. The process uses a screw extruder (particularly a twin screw) to fill packages.

U.S. Pat. No. 6,261,579 to Roulier et al for L'Oreal describes the use of compression and extrusion in a twin screw extruder for the formation of a cosmetic hydrating gel. The gel is composed of 20% or more water soluble or hydrophilic gelling agents in the presence of water.

U.S. Pat. No. 6,045,814 to Roulier et al for L'Oreal describes rigid gels containing at least 20% of one or more hydrophilic gelling agents. The gels are obtained in the presence of water by mixing, blending, compression and extrusion in a twin-screw extruder. This reference includes pigment in the composition later removed in U.S. Pat. No. 6,261,579.

U.S. Pat. No. 5,490,979 to Kasat et al for Colgate Palmolive describes composition and method of manufacture of a clear stick antiperspirant. This reference describes a method which uses a twin screw extruder to create separate mixing chambers where temperatures can be controlled and prevent degradation of heat sensitive ingredients.

PCT Application 99/07429 to Allan et al for Hindustan Lever Ltd. describes a compartmented progressive pitched screw which acts as mixer/delivery/temperature controller, and delivers a uniform product to be filled into standard AP containers at temperatures between 0 and 3 degrees below the melt point of the composition. Benefits are uniformity of active content obtained by eliminating sedimentation, and an ability to add temperature sensitive ingredients late in the process.

U.S. Pat. No. 4,688,609 to Diaz for Fluid Packaging Co. describes a system for injecting molten product into deodorant stick containers with automatically dispensing metered amounts of viscous product in assembly line fashion into a series of containers.

PCT Application 01/02824 to Allan et al for Hindustan Lever Ltd. describes the application of the filling apparatus in PCT 99/07429, to the production and filling of soft solid product formulations via batch or continuous means, with screw extrusion filling under pressure.

U.S. Pat. No. 4,678,420 to Inoue for Inoue-Japax Research describes an injection molding method for plastic melts and formation of finished units using a feed screw and piston, under pressure and with temperature control.

U.S. Pat. No. 6,338,840 to Allan, et al for Unilever describes a process and apparatus for the production of an antiperspirant and/or deodorant product by a continuous process involving injection molding.

Specific patents that disclose extrusion as a method of producing stick deodorants and antiperspirants include the following: U.S. Pat. Nos. 6,161,579 and 6,045,814 to Roulier, et al. disclose water-soluble gels which are kept at elevated temperature through the extrusion process in the 60–100° C. range. PCT Application WO 00/19861 to Allan et al. for Lever (see also WO 00/41169 A1) discloses a process using temperatures between 0–3° C. below the melt point of the composition while filling containers. The apparatus described is best described as a screw feeder with temperature control rather than an extruder that compresses the composition. U.S. Pat. No. 5,316,712 to Ono et al, discloses an extrusion/injection molding of an oil and powder mixture into a mold to form a cosmetic. U.S. Pat. No. 4,688,609 to Diaz discloses a device for filling sticks using a piston and air actuated plunger to control flow and fill weight of molten material. U.S. Pat. No. 4,897,236 to Rabiger et al, discloses a process and apparatus that can be used for extruding rubber.

In other non-antiperspirant/deodorant fields, references of interest include U.S. Pat. No. 5,316,712 to Ono et al for JO Cosmetics which describes an injection molding method for making cosmetics using a piston to force a molten composition into a die and cooling it there, then discharging the product from the die for packaging; and U.S. Pat. No. 4,897,236 to Rabiger et al for Herman Berstorff Maschinenbau which describes a method and apparatus for the continuous manufacture of rubber or polymer based mixtures containing additives. The ingredients for the mixture are fed into a twin screw extruder and masticated and homogenized therein. Recycling is described.

These previous attempts are not completely satisfactory in accomplishing the objects of the present invention since they require elevated temperatures and a prescribed package form in which to deposit the product while it is hot. Thus, the objects of the invention include having the ability to extrude the stick formula ingredients at temperatures well below the melting point of the formula, and being able to create solid sticks without requiring a package form to shape the product. Further advantages of the invention include (1) greater flexibility in packaging the final product; (2) increased uniformity in product since solid products are less likely to have the individual ingredients settle out during the process; (3) reduction or elimination of voids and cavities, shrinkage and cracking since relatively little cooling takes place; (4) increased ability to use volatile products that would otherwise be lost because of heat; and (5) greater ability to use temperature sensitive materials that might otherwise degrade because of exposure to elevated temperatures (for example, fragrances). Yet another advantage of the invention is (6) the ability to make antiperspirants and/or deodorants which have colored striations, or other aesthetics not possible in other conventional manufacturing routes for molten sticks.

SUMMARY OF THE INVENTION

This invention utilizes mechanical means of mixing, homogenizing and extruding a stick formulation at temperatures well below the melting point of the formula. In general no heat is added (except that created by mechanical energy transferred to the product, and possible warming of the extrusion barrel for some formulas) and the ingredients are blended or homogenized into a single mixture. The resulting sticks are in solid form and do not require a package or other molding device to shape the solid product. The resulting sticks can be inserted into a rigid plastic container, a film wrapper, or a refill unit for a specialized refill package, for dispensing. This ability to form a solid stick without a mold or package, also allows alternative packaging forms which are less expensive and more environmentally friendly such as wrappers (which could be used in developing markets to reduce packaging costs which typically run 40–60% of total product cost); or refill packs, where a convenient refill unit can be inserted into a reusable refill dispenser to reduce purchase cost.

This invention provides a process for extruding a solid stick that is made of blends of material that are worked to uniformity by mechanical means for mixing, homogenizing and extruding the stick formula ingredients at temperatures well below the melting point of the formula. The ability to make products such as antiperspirants and/or deodorants that have a burden of assimilating solids added as particulates is a very useful feature of the invention.

DETAILED DESCRIPTION OF THE DRAWINGS

Figure 1:
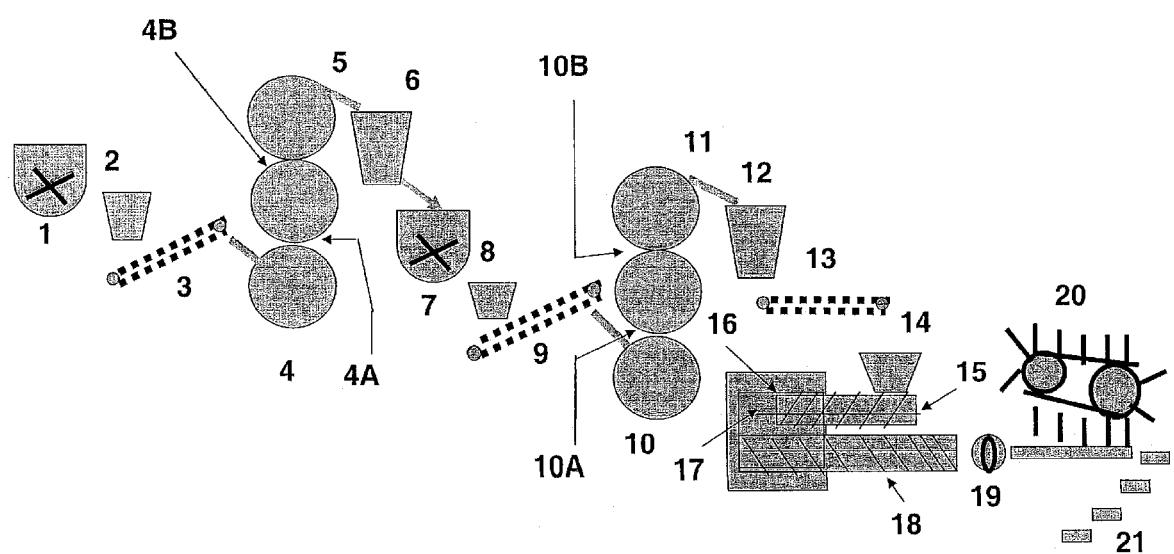
FIG. 1 shows a diagram of how the process equipment is arranged.

In FIG. 1, there is shown a first amalgamator 1 which is a horizontal mixing unit (preferably made from 304/316 stainless steel such as is available from Mazzoni Co., Milan Italy) which combines the organic and plastic structuring agents as powdered and flaked materials into a well mixed blend of solids. The blended materials from the first amalgamator 1 goes into a first surge hopper 2 (also made from 304/316 stainless steel) which controls the flow of the product onto a first flighted belt 3. The first belt 3 feeds the blend into a first roll mill 4 between rollers that result in the blend being homogenized and then moved to the top of the roll mill. The blend is removed from the top roll of the first roll mill 4 by a first scraper 5. The scraping action results in the blend being dropped into a second surge hopper 6. The second surge hopper 6 feeds the blend into a second amalgamator 7 wherein other ingredients are added, both liquid and solid/powders, as well as fragrance. The blend from the second amalgamator 7 is then dropped into a third surge hopper 8 which controls the flow of the blend onto a second flighted belt 9 and feeds the blend into a second roll mill 10, again for homogenization purposes. The blend is removed from the top roll of the second roll mill 10 by a second scraper 11. The scraping action results in the blend being dropped into a fourth surge hopper 12 which feeds the blend onto a third flighted belt 13 and downward into an extruder assembly. The extruder assembly comprises a feed hopper 14 which feeds an inwardly moving worm 15 which forces the blend through a perforated plate or mesh screen (particularly 10 mesh) 16, an extruder chamber 17 and an outwardly moving progressively flighted worm 18. The extruder assembly can be a multiple stage single or double screw extruder. At the discharge end of the worm 18 is positioned a compression orifice plate 19 which defines the shape of the extruded product. After the plate 19 is a cutting means 20 to form the products 21 as discrete units also called billets. The products may be cut to any length desired to fit into packaging or to be wrapped separately. The billets may be used as is or subjected to further steps. For example, the billets may be compressed or microwaved to improve the properties. Optionally an embosser (not shown) may be used to imprint a design on the units with compression, or to attach them to a package part required to make them refill units for use with refill packages. Note the characters 4A and 10A for gaps.

Both of the roll mills are a series of 3–5 tightly spaced rollers being spaced approximately 0.5–3.0 mm apart with the usual orientation of having the spaces being of decreasing size as the product moves upward between the rollers. The temperature gradient allows transfer of the blended materials to occur from one roller to the next in the assembly. Speeds of the rollers are adjusted so that little or no heat is transferred. In one embodiment, no heating or cooling is used at all. In each case where the roll mills are used, the blended materials are homogenized, pelletized, mixed, or subjected to refining plodding.

In another embodiment one or all of the roll mills can be replaced by a modified extruder assembly comprising elements 14–18, with a perforated plate replacing the orifice plate 19. Note that the terms blended material and blend can be used interchangeably.

A post extrusion treatment option may also be used in which the product may be subjected to a one of the following heating steps. First option—cut billets from the process are subjected to a thermal environment sufficient to create a smoother surface. Second option—Extruded product either before or after cutting is subjected to microwave treatment sufficient to smooth the surface and/or modify the texture of the product. Such microwave treatment may be used to modify the texture and/or unit structure; and improve cup retention, payout and application aesthetics.

The final form of the unit can be packaged as is in a conventional plastic container, or wrapped for consumer use, or affixed to a mechanism that would allow it to become a refill for a package having an appropriate shape for the unit.

DETAILED DESCRIPTION OF THE INVENTION

The invention comprises a process for forming a free standing antiperspirant or deodorant solid stick product using particulate and fluid materials that are combined by means of amalgamation, homogenization, compaction and extrusion below the melting temperature of said product and extruded by mechanically working the particulate and fluid materials comprising the steps of:

(A) selecting a mixture of particulate and fluid materials as:
 (a) 16–35 weight % volatile and non-volatile silicone, provided that the composition contains at least about 16 weight % volatile silicone;
 (b) 10–30 weight % (particularly 25–30%) of a structuring agent with a melting point $\leq 80$ degrees C. selected from the group consisting of C16–20 fatty alcohols (especially stearyl alcohol or sorbitol); C16–C22 fatty acids with or without an hydroxy substitution; C16–C22 fatty ethers; waxes with a melting point $\leq 80$ degrees C. (for example, beeswax, castor wax with a melting point less than or equal to 80 degrees C.); paraffins having a melting point of less than 80 degrees C.; glycerin; vegetable oils (for example, soybean oil); hydrogenated oils; and mixtures of any of the foregoing, selected to form the desired hardness;
 (c) 8–30 weight % a particulate material having a particle size less than 10 microns and selected from the group consisting in type and amount of 8–20 weight % (particularly 12–15%) talc; 8–20 weight % clays (for example, bentonites, attapulgites, and smegtites); 8–20 weight % zeolites; 1–12 weight % superabsorbent having little or no tack upon wetting (for example, a superabsorbent polymer selected from the group consisting of starch graft homopolymers and copolymers of poly(2-propenamide-co-2-propenioic acid) sodium salt (such as WATERLOCK® A 180 from Grain Processing Corp., Muscatine, Iowa); 1–8 weight % low melting point polyethylene;

(d) an effective amount of active ingredient such as an antiperspirant active to provide a deodorant and/or an antiperspirant (for example, an aluminum-zirconium glycine complex (such as 16–25 weight %, particularly 22–23 weight % if an antiperspirant is required; or 10–15% if only a deodorant is required)); and (e) optionally 2.5–5 weight % Japan wax (for example, AMS C30 from Frank B. Ross Co., Jersey City, N.J.); and (B) performing a process comprising the steps of:

(a) mixing and combining the structuring agents into a well mixed blend of solids using a first mixing means (examples of suitable mixing equipment include, but are not limited to, Amalgamator, Hobart, Ross, Agi, Lee, Ribbon, Lodigi, or other powder mixing devices);

(b) feeding the mixture into a first homogenizing means;

(c) homogenizing the mixture (for example with homogenizing means such as a roll mill with multiple rollers spaced about 0.5–3.0 mm apart, or a single or twin screw refining plodder, or other suitable device);

(d) mixing the homogenized mass with particulate, active, fragrance and other remaining ingredients in a second mixing means (for example, of the type described in part (a);

(e) homogenizing the mixture of (d) with a second homogenizing means (for example selected from the same type of equipment as in part (c);

(f) extruding the complete mixture to obtain a uniform, solid, cohesive extrudate;

(g) cutting the extrudate into billets of a selected length; and (h) forming unit products, these individual units have a cross section determined by the shape of the extrusion plate and whose length can be varied as needed);

Optional additional steps include:

(i) compressing the billet to a preselected shape;

(j) embossing the billet for more precise sizing and shaping, for example, by using a press, with pin or box dies, to create a more precise shape, along with the compression;

(k) treating the billet with microwaves before it is cut or the units after they are cut and before or after they are pressed (since microwave treatment can modify the properties of the stick in favorable ways for structure, payout and application aesthetics).

The product formed will have a hardness of 50–90 Dietert Green hardness units, "B" scale (DISA Georg Fischer +GF+). This hardness tester is available as No. 42-GHT(B) from Ridsdale & Company LTD., Newham Hall, Newby, Middlesbrough, England.

The current invention relies on mechanical working of the ingredients to achieve a formed stick at the outlet of the extruder without need for a mold/die to act as a form while solidifying a melt. The process of the current invention uses physical mixing and compression via a plodder, or similar device, to achieve the intimate contact and structure required to produce the final stick. The basic process involves combining all the organics (waxes, alcohols, and other plastic ingredients) by means of a roll mill, or other ribbon, or pelletizing devices. This step is repeated two or more times to insure that all of these ingredients are uniformly well mixed and fully plasticized. The resulting material is then combined with all of the fillers and liquids that make up the formulation, including fragrance. The mixture is then amalgamated, homogenized by either pelletizing or passing through a roll mill, to create a mixture that can be plodded. The resulting ribbons, pellets, or amorphous mass must be free flowing enough to feed the hopper of the plodder so the worm can transfer this material without bridging. For some formulations the material may require some mechanical assistance to feed the worm without bridging in the feed hopper 14. The plodder can be a single worm or a multiple worm unit. Various screens or plates (for example, 10 mesh) can be inserted to change the compression generated by the individual plodder stages.

The formulation plays a key role in determining what compression and other processing is required to produce a stick with appropriate consumer use characteristics.

The volatile silicones may be selected from linear and cyclic types. Linear volatile methyl siloxanes ("VMS") have the formula $(CH_3)_3 SiO\{(CH_3)_2 SiO\}_y Si(CH_3)_3$. The value of y is 0–5. Cyclic VMS have the formula $\{(CH_3)_2 SiO\}_z$. The value of z is 3–6. Preferably, these volatile methyl siloxanes have boiling points less than about 250 degrees C. and viscosities of about 0.65–5.0 centistokes ($mm^2/s$). Representative linear volatile methyl siloxanes (I) are hexamethyldisiloxane (MM) with a boiling point of 100 degrees C., viscosity of 0.65 $mm^2/s$, and formula $Me_3 SiOSiMe_3$; octamethyltrisiloxane (MDM) with a boiling point of 152 degrees C., viscosity of 1.04 $mm^2/s$, and formula $Me_3 SiOMe_2 SiOSiMe_3$; decamethyltetrasiloxane ($MD_2$ M) with a boiling point of 194 degrees C., viscosity of 1.53 $mm^2/s$, and formula $Me_3 SiO(Me_2 SiO)_2 SiMe_3$; dodecamethylpentasiloxane ($MD_3$ M) with a boiling point of 229 degrees C., viscosity of 2.06 $mm^2/s$, and formula $Me_3SiO(Me_2SiO)_3 SiMe_3$; tetradecamethylhexasiloxane ($MD_4$ M) with a boiling point of 245 degrees C., viscosity of 2.63 $mm^2/s$, and formula $Me_3SiO(Me_2SiO)_4 SiMe_3$; and hexadecamethylheptasiloxane ($MD_5$ M) with a boiling point of 270 degrees C., viscosity of 3.24 $mm^2/s$, and formula $Me_3 SiO(Me_2 SiO)_5 SiMe_3$. Representative cyclic volatile methyl siloxanes (II) are hexamethylcyclotrisiloxane ($D_3$) a solid with a boiling point of 134 degrees C. and formula $\{(Me_2)SiO\}_3$; octamethylcyclotetrasiloxane ($D_4$) with a boiling point of 176 degrees C., viscosity of 2.3 $mm^2/s$, and formula $\{(Me_2) SiO\}_4$; decamethylcyclopentasiloxane ($D_5$) with a boiling point of 210 degrees C., viscosity of 3.87 $mm^2/s$, and formula $\{(Me_2)SiO\}_5$; and dodecamethylcyclohexasiloxane ($D_6$) with a boiling point of 245 degrees C., viscosity of 6.62 $mm^2/s$, and formula $\{(Me_2)SiO\}_6$.

Non-volatile silicones may be selected from the group consisting of PEG/PPG-18/18, cyclopentasiloxane and/or cyclopentasiloxane crosslinked, and polydimethylsiloxane liquid at a viscosity between 20–12,500 cst. This is true for this invention since these are nonvolatiles as compared to cyclomethicones. The cyclopentasiloxanes and polymers are nonvolatile even though when filled with cyclomethicone they become more volatile.

One particular silicone ingredient includes 0–5 weight % of a fluidizer (Fluid AP from Dow Corning) a volatile silicone.

Various antiperspirant active materials can be utilized according to the present invention. These include conventional aluminum and aluminum/zirconium salts, as well as aluminum/zirconium salts complexed with a neutral amino acid such as glycine, as known in the art. See each of European Patent Application Number. 512,770 A1 and PCT case WO 92/19221, the contents of each of which are incorporated herein by reference in their entirety, for disclosure of antiperspirant active materials. The antiperspirant active materials disclosed therein, including the acidic antiperspirant materials, can be incorporated in the compositions of the present invention if they are soluble in the active phase. Suitable materials include (but are not limited to) aluminum chlorides (various types including, for example, anhydrous form, hydrated form, etc.), zirconyl hydroxychlorides, zirconyl oxychlorides, basic aluminum chlorides, basic aluminum chlorides combined with zirconyl oxychlorides and hydroxychlorides, and organic complexes of each of basic aluminum chlorides with or without zirconyl oxychlorides and hydroxychlorides and mixtures of any of the foregoing. These include, by way of example (and not of a limiting nature), aluminum chlorohydrate, aluminum chloride, aluminum sesquichlorohydrate, aluminum chlorohydrol-propylene glycol complex, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum dichlorohydrate, aluminum chlorohydrex PG, aluminum chlorohydrex PEG, aluminum dichlorohydrex PG, aluminum dichlorohydrex PEG, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing. The aluminum-containing materials can be commonly referred to as antiperspirant active aluminum salts.

Particular types of antiperspirant actives include aluminum zirconium trichlorohydrex and aluminum zirconium tetrachlorohydrex either with or without glycine. A particular antiperspirant active is aluminum trichlorohydrex gly such as AZZ-902 SUF (from Reheis Inc., Berkley Heights, N.J.) which has 98% of the particles less than 10 microns in size.

Antiperspirant actives can be incorporated into compositions according to the present invention in amounts in the range of 0.1–25% of the final composition, but the amount used will depend on the formulation of the composition. For example, at amounts in the lower end of the broader range (for example, 0.1–10% on an actives basis), a deodorant effect may be observed. At lower levels the antiperspirant active material will not substantially reduce the flow of perspiration, but will reduce malodor, for example, by acting as an antimicrobial material. At amounts of 10–25% (on an actives basis) such as 15–25%, by weight, of the total weight of the composition, an antiperspirant effect may be observed. In particular, salts with low metal to chloride ratio such 0.1–25 weight % of an antiperspirant active having a low metal to chloride ratio in the range of 0.9–1.3 may be used.

Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as tin or titanium salts used alone or in combination with aluminum compounds (for example, aluminum-stannous chlorohydrates), aluminum nitratohydrate and its combination with zirconyl hydroxychlorides and nitrates, can be incorporated as an antiperspirant active ingredient in antiperspirant compositions according to the present invention.

Preferred antiperspirant actives that can be incorporated in the compositions of the present invention include the enhanced efficacy aluminum salts and the enhanced efficacy aluminum/zirconium salt-glycine materials, having enhanced efficacy due to improved molecular distribution, known in the art and discussed, for example, in PCT No. WO92/19221, the contents of which are incorporated by reference in their entirety herein. Particular actives include Westchlor A2Z 4105 aluminum zirconium tetrachlorohydrex gly propylene glycol complex, (from Westwood Chemical Corporation, Middletown, N.Y.); Westchlor ZR 35B aluminum zirconium tetrachlorohydrex gly, and Rezal 36 GP and AZP 902 aluminum zirconium tetrachlorohydrex gly both from Reheis, Berkeley Heights, N.J. as well as Rezal AZZ 908 from Reheis. In general, the metal:chloride mole ratio is in the range of 2.1–0.9:1 for such salts.

In one particular type of salt of interest, an aluminum zirconium tetra salt with glycine is used wherein aluminum zirconium tetrachlorohydrex glycine salt having a metal to chloride ratio in the range of 0.9–1.2:1 (especially in the range of 0.9–1.1:1 and, more particularly in the range of 0.9–1.0:1); and a glycine:zirconium mole ratio greater than 1.3:1, particularly greater than 1.4:1. This type of salt may be made in a variety of ways such as the following.

Mixtures of actives can also be used, provided a suitable amount of low RI material is used to achieve a satisfactory product.

Antiperspirant actives can be incorporated into compositions according to the present invention in amounts in the range of 7–25% (on an anhydrous solids basis), preferably 7–20%, by weight, of the total weight of the composition. The amount used will depend on the formulation of the composition. At amounts at the higher end of the range (especially in a range of 9–20% or 9–25%, a good antiperspirant effect can be expected. As noted above, the active is preferably included in the compositions of the invention by premixing the active with water and possibly small amount of propylene glycol.

Additionally, surfactants may be included in the compositions of the invention. Illustratively such surfactants include alkanolamides (such as N-alkyl pyrrolidone), ethoxylated amides (for example, the polyethylene glycol amide of tallow acid that conforms generally to the formula RC(O)—NH—(CH$_2$CH$_2$O)$_n$H where RCO— represents the fatty acids derived from tallow and n has an average value of 50 (also called PEG-50 tallow amide)); amine oxides (for example, cocamidopropylamine oxide); ethoxylated fatty acids (for example, the polyethylene glycol diester of stearic acid that conforms generally to the formula CH$_3$(CH$_2$)$_{16}$C (O)—(OCH$_2$CH$_2$)$_n$O—C(O)(CH$_2$)$_{16}$CH$_3$ (also called PEG-8 distearate)); ethoxylated glycerides (for example, a polyethylene glycol derivative of Castor Oil with an average of 4 moles of ethylene oxide (also called PEG-4 castor oil)); glycol esters (for example, propylene glycol ricinoleate); monoglycerides (for example, glycerol myristate); polyglyceryl esters (for example, polyglyceryl-4 oleyl ether); polyhydric alcohol esters and ethers (for example, sucrose distearate); sorbitan/sorbitan esters (for example, sorbitan sesquiisostearate); triesters of phosphoric acid (for example, trioleth-8 phosphate (a material which is predominantly the triester of phosphoric acid and ethoxylated oleyl alcohol with an average of 8 moles of ethylene oxide)); ethoxylated lanolin (for example, a polyethylene glycol derivative of Lanolin with an average of 20 moles of ethylene oxide (also called PEG-20 lanolin)); propoxylated polyoxyethylene ethers (for example, the polyoxypropylene, polyoxyethylene ether of cetyl alcohol that conforms generally to the formula $CH_3(CH_2)_{14}CH_2(OCH(CH_3)CH_2)_x(OCH_2CH_2)_yOH$ where x has an average value of 5 and y has an average value of 20 (also called PPG-5 ceteth-20)); and alkylpolyglycosides (for example, lauryl glucose). The surfactant (or surfactant blend) includes non-ionic compounds, and can also include blends thereof with cationic (for example, the polyethylene glycol amine of tallow acid that conforms generally to the formula $R-NH-(CH_2CH_2O)_nH$ (n=15, also called PEG-15 tallow amine)) or anionic (for example, sodium lauroyl laurate which is the sodium salt of the lauric acid ester of lauric acid) surfactants.

Some of the ingredients used have multifunctional properties in terms of being structuring agents, texturizers, emollients or moisturizing agents. For example, petrolatum falls into at least three categories (moisturizer, fluidizer and texturizer). For clarification of function the following terms may be helpful in understanding this invention. A texturizer is a material that provides the necessary product application aesthetics expected by the consumer, for example, soft/smooth feel as the stick is applied, good glide characteristics in use, etc. A fluidizer facilitates ease of blending and uniformity of the organic and powdered phases when combined in the process, efficiently producing a homogenous blend of these formula components during processing. Moisturizers are compounds that provide the necessary skin conditioning and protection from dryness during product use. Essentially they form a coating on the skin to hinder moisture loss from the application surface and thus minimize resulting dryness.

More particularly, one embodiment of the invention comprises a cold process for making stick products comprising combining the following three components:

(A) 16–35 weight % volatile and non-volatile silicone (especially D5 and/or D6 cyclomethicone as the volatile silicone), provided that the composition contains at least about 16 weight % volatile silicone.

(B) at least 25–30 weight % of a structuring agent comprising two or more of the following ingredients: C16–C22 fatty alcohols; C16–C22 fatty acids; C16–C22 fatty ethers; and waxes having a melting point of less than 80 degrees C.; and paraffins having a melting point of less than 80 degrees C.;

(C) 8 to 30 weight % of particulate material selected from the group comprising talcs (8–20%), clays (8–20%), low melting point (mp in the range of 45–75 degrees C.) polyethylenes (0–8%); superabsorbents such as 1–12% weight of a superabsorbent powder with little or no tack upon wetting such as, for example, a superabsorbent polymer selected from the group consisting of starch graft homopolymers and copolymers of poly(2-propenamide-co-2-propenioic acid) sodium salt;

(D) antiperspirant actives (effective amount such as 10–15% for deodorant only products and 20–25% for antiperspirant products); and (E) the remainder being a texturing material selected from the group consisting of liquid petrolatum with a melting point less than 60 degrees C.; C12–15 alkyl benzoates such as FINSOLV TN; silicones such as Fluid AP from Dow Corning Corp. (Midland, Mich.); non-volatile silicones such as cyclopentasiloxane and crosslinked cyclopentasiloxane available as DC 9040, 9041, and/or 9045, or Shintsu KSG 15; and volatile silicones such as DC 245 and 345 Fluid from Dow Corning; and PEG/PPG-18/18, and dimethicones such as polydimethylsiloxane; dimethicone copolyols such as DC200 and its various viscosity variants. Silicones of the type represented by DC 245 and DC 345 are volatile silicones which are cyclomethicones. In addition, these cyclomethicones are part of the composition of elastomers which can be used in these formulations with great benefit. For the purposes of this patent elastomers are both volatile and non-volatile silicones. Due to their "solid" form and this dual nature of volatility, they represent a separate class of materials that may be used in the category of particulate matter.

Silicone elastomers such as (a) a dimethicone/vinyldimethicone crosspolymer composition made by reacting (in the presence of a platinum catalyst) a polymethylhydrogensiloxane with an alpha, omega-divinylpolydimethyl siloxane for which the dimethicone/vinyldimethicone crosspolymer composition (1) is used at a concentration of 4–10% in cyclomethicone (particularly 4–7%, and, more particularly, 4–6.5%) (for example, where the cyclomethicone is a D4 or D5 cyclomethicone), (2) has a refractive index in the range of 1.392–1.402 at 25 degrees C., and (3) has a viscosity in the range of 0.013–1×10$^4$ Pascal seconds (for example, one particular elastomer of interest is KSG-15 silicone elastomer from Shin-Etsu Silicones of America (Akron, Ohio);

(b) a cyclomethicone (and) dimethicone crosspolymer made with an =Si—H containing polysiloxane and an alpha, omega-diene of formula $CH_2=CH(CH_2)_xCH=CH_2$, where x=1–20, to form a gel by crosslinking and addition of =Si—H across double bonds in the alpha, omega diene, which crosspolymer has a viscosity in the range of 50,000–3,000,000 centipoise (particularly 100,000–1,000,000; more particularly 250,000–450,000 centipoise; and most particularly 350,000 centipoise), preferably with a nonvolatiles content of 8–18% (particularly 10–14% and most particularly 12–13%) in cyclomethicone (for example a D4 or D5 cyclomethicone), (an example of such a crosspolymer composition being DC-9040 from Dow Corning Corporation (Midland, Mich.) with other types of such crosspolymers (also called elastomers) being described in U.S. Pat. No. 5,654,362 incorporated by reference herein as to the description of such polymers and methods of making such polymers);

Particular examples of suitable elastomers are SFE 167, a cetearyl dimethicone/vinyl dimethicone crosspolymer from GE Silicones (Waterford, N.Y.); SFE168, a cyclomethicone (and) dimethicone/vinyl dimethicone crosspolymer from GE Silicones; vinyl dimethicone crosspolymers such as those available from Shin Etsu Silicones of America (Akron, Ohio) under trade names KSG-15 (cyclomethicone (and) dimethicone/vinyl dimethicone crosspolymer), KSG-16 (dimethicone (and) dimethicone/vinyl dimethicone crosspolymer), KSG-17 (cyclomethicone (and) dimethicone/vinyl dimethicone crosspolymer), KSG-18 (phenyl trimethicone (and) dimethicone/phenyl vinyl dimethicone crosspolymer); and KSG-20 (dimethicone copolyol crosspolymer; dimethicone/vinyl dimethicone crosspolymer from Dow Corning Corporation (Midland, Mich.) under trade name Dow Corning 9506 Cosmetic Powder, DC-9040, DC-9041, DC-9045 elastomers in cyclomethicone from Dow Corning; and a mixture of cyclomethicone and stearyl-vinyl/hydromethylsiloxane copolymer available from Grant Industries, Inc. (Elmwood Park, N.J.) under the trade name Gransil SR-CYC.

The process of the invention is carried out at temperatures that are well below the melt point of the formulation and, more particularly, do not exceed about 60 degrees C. The mechanical energy supplied by the mixing, homogenization and extrusion units, provides some mechanical heat as well as mixing and compression. This heat serves to plasticize or weld the various components in the formula together. During this process milling or other mechanical means are used to homogenize the organic portion of the formula. This is followed by mechanical mixing with the other formula ingredients, and then followed by further mixing, using milling or other mechanical means. The resulting mixture is then extruded/plodded through an orifice plate to create the desired shape for the final antiperspirant or deodorant stick. The extrusion is cut to length for the final cosmetic stick.

Mixing is effected that can be performed equally well by an Amalgamator, Sigma mixer, Agi, Lee, Hobart, Ross, and Ribbon mixer, or any other mixer of this type/class of mixers provided that the mixer is capable of handling somewhat sticky ingredients but one that can work powders and liquids into a relatively homogeneous mass, while emptying the ingredients almost completely from the mixer once the mixture is completed.

Milling, also referred to as "working the mixture" can be performed equally well by a roll mill, a twin screw extruder, a single screw extruder, extruders of both types with or without screens, with or without perforated plates, or any other type/class of equipment that works mixtures of solids and semi solids. Effective homogenization can be identified when a small sample (1.0 gram) is representative of the entire formulation that was fed to the homogenizing unit has a uniform texture (except for any striations that are desired.

Extrusion of the milled mixture can be performed equally well by a twin screw extruder, a single screw extruder, extruders of both types with or without screens, with or without perforated plates, or a Warner & Fleighterer refining system, or any other type/class of equipment that works mixtures of solids and semi-solids. The unit must have sufficient compression to form a continuous extrusion that does not have physical cracks or fissures caused by starting and stopping the extrusion screws.

When striations or other post-added aesthetics are desired they can be incorporated into the extruded stick by an injection stream of color that uses glycerin, propylene glycol or other delivery vehicles that can solubilize or suspend a pigment or dye in it to provide the desired color stripes or aesthetics. The carrier should have limited ability to permeate the stick, as this would tend to diffuse the color evenly throughout the stick over time. If this were to happen the stick would become a uniform color over time and differentiation of striations would not be visible.

An alternative method for creating striations is to form the complete base formula and then color portions of it before feeding it to the extruder/plodder. This method decreases the possibility of diffusion of the color after the stick is made.

EXAMPLES

The following Examples are offered as illustrative of the invention and are not to be construed as limitations thereon. In the Examples and elsewhere in the description of the invention, chemical symbols and terminology have their usual and customary meanings. In the Examples, as elsewhere in this application, values for molecular weights are averages. Temperatures are in degrees C. unless otherwise indicated. The amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7$^{th}$ ed. 1997).

Example 1

Antiperspirant

The following organic ingredients were combined as powders and then milled (note that the same result can be achieved by extrusion, compression, pelletizing) using a three roll mill and passing the material through it three times: 25.00% stearyl alcohol, 10.00% castor wax, 8.00% polyethylene (MP-130 from Equistar Chemicals, L.P., Houston, Tex.). This results in a ribbon-like or flake intermediate form. The rest of the ingredients are then added to these ribbons and mechanically mixed. These include 22.25% antiperspirant active (REACH 36 trisalt from Reheis); 12.75% talc (Ultra Chemical, Redbank, N.J.); 14.50% cyclomethicone (DC 245 from Dow Corning, Midland, Mich.); 6.50% octododecanol; and 1.00% fragrance. Mixing can be a physical stirring, cutting, amalgamation (as in 1 and 7 in FIG. 1, or any other means that will bring all the ingredients into intimate contact with each other. This resulting mixture is milled as in 4 and 10 in FIG. 1 (again the same results can be achieved by the means mentioned above) creating a ribbon/amorphous mass that can be fed to the plodder. This intermediate material is fed to a pitched worm plodder (15–18 in FIG. 1) with refining screen (16 in FIG. 1) and cutter (20 in FIG. 1). The plodder blank is extruded through an orifice (19 in FIG. 1) equal in size and shape to the package that will contain the extruded material. This formula demonstrates the value of octodecanol as an ingredient, which improves stick properties of payout and application aesthetics. It was found that increasing the octodecanol content from 6 to 10% there is an improvement in application aesthetics.

Example 2

Antiperspirant

The method of Example 1 can be repeated using the following ingredients as the organics: 25% stearyl alcohol; 8% castor wax (MP 70 from Acme-Hardesty, Blue Bell Pa.); and 8% polyethylene. The remaining ingredients include 13.50% cyclomethicone (DC245); 5% C12–15 alkyl benzoate; 5% Fluid AP (a volatile silicone from Dow Corning); 22.00% antiperspirant active (REACH 36 trisalt from Reheis); 10.00% talc (Ultra Chemical); 2.5% petrolatum and 1.00% fragrance. It was found that the use of petrolatum and/or mineral oil was an inexpensive way of improving stick performance attributes such as payout/use-up and skin feel specifically.

Example 3

Deodorant

In the manufacture of extruded deodorant formulations the following ingredients are combined as and then milled (note that the same result can be achieved by extrusion, pelletizing, compression) using a three roll mill and passing the material through it three times:

| | |
|---|---|
| 80/20 Tallow/Coco Soap Chip | 46.50 |
| Propylene Glycol | 23.64 |
| Water | 13.97 |
| Diethylenetriamine Pentaacetic Acid-40% | 0.05 |
| Citric Acid-50% Solution | 0.42 |
| 99% CP Glycerin for Toilet Articles | 4.81 |
| 99% Triethanolamine | 0.84 |
| Distilled Coconut Oil Fatty Acids | 1.27 |
| Brine-25% Solution | 1.31 |
| Sorbitol-70% Solution | 7.19 |
| Total | 100.00 |

Soap pellets or flakes of an 80% tallow, palm oil, palm stearin or combination of these C16–C18 triglycerides and 20% coconut oil, palm kernel oil, palm kernel olein or combination of these lauric (C12) triglycerides, having a moisture level of 8%–25%, are combined with propylene glycol, 99% C.P. Glycerin, 99% Triethanolamine, Distilled Coconut Oil fatty acids, brine solution and 70% sorbitol in the amalgamators (1 and 7, FIG. 1) or any other means that will bring these ingredients into intimate contact. This resulting mixture (blend) is then milled (roll mills 4 and 10, FIG. 1) to create a ribbon/amorphous mass that can be fed to the extruder chamber (also called a plodder) (17 in FIG. 1). The rest of the ingredients are then added to these ribbons and mechanically mixed. These include: Diethylenetriamine Pentaacetic Acid—40% and Citric Acid—50% solution. Mixing can be a physical stirring, cutting, amalgamation (as in 1 and 7 in FIG. 1), or any other means that will bring all the ingredients into intimate contact with each other. This resulting mixture is milled as in 4 and 10 in FIG. 1 (again the same results can be achieved by the means described above) creating a ribbon/amorphous mass that can be fed to the plodder. This intermediate material is fed to a pitched inwardly moving worm (15 in FIG. 1) with mesh screen (16 in FIG. 1) and cutter (20 in FIG. 1). The plodder blank is extruded through an orifice plate (19 in FIG. 1) equal in size to the package that will contain the extruded material.

What is claimed is:

1. A process for forming a free standing antiperspirant or deodorant solid stick product using particulate and fluid materials that are combined by means of amalgamation, homogenization, compaction and extrusion at a temperature below the melting temperature of said product and extruded by mechanically working the particulate and fluid materials, wherein the process comprises the steps of:
(A) selecting a mixture of particulate and fluid materials as:
  (a) 16–35 weight % volatile and non-volatile silicone, provided that the composition contains at least about 16 weight % volatile silicone;
  (b) 10–30 weight % of a structuring agent with a melting point ≦80° C. selected from the group consisting of C16–20 fatty alcohols; C16–C22 fatty acids with or without an hydroxy substitution; C16–C22 fatty ethers; waxes with a melting point ≦80 degrees C.; paraffins having a melting point of less than 80 degrees C.; glycerin; vegetable oils; hydrogenated oils; and mixtures of any of the foregoing sufficient to form a stick product having a hardness of 50–90 Dietert Green hardness units, on a B scale;
  (c) 8–30 weight % a particulate material having a particle size less than 10 microns and selected from the group consisting in type and amount of 8–20 weight % talc; 8–20 weight % clays; 8–20 weight % zeolites; 1–12 weight % superabsorbent having little or no tack upon wetting; 1–8 weight % low melting point polyethylene;
  (d) an effective amount of an antiperspirant active ingredient sufficient to provide a deodorant and/or an antiperspirant; and
  (e) Optionally 2.5–5 weight % Japan wax; and
(B) performing a process comprising the steps of:
  (a) mixing and combining the structuring agents into a well mixed blend of solids;
  (b) feeding the mixture into a first homogenizing means;
  (c) homogenizing the mixture;
  (d) mixing the homogenized mass with particulate, active, fragrance and any other remaining ingredients in a second mixing means;
  (e) homogenizing the mixture of (d) using a second homogenizing means;
  (f) extruding the complete mixture to obtain a uniform, solid, cohesive extrudate; and
  (g) cutting the extrudate into billets of a selected length; and
  (h) forming unit products.

2. The process as claimed in claim 1 comprising one or more additional steps selected from the group consisting of:
  (i) compressing the billet to a preselected shape;
  (j) embossing the billet with compression; and
  (k) treating the billet with microwaves either before or after final unit products are formed.

3. The process as claimed in claim 1 comprising placing the stick product in a refillable container.

4. The process as claimed in claim 1 wherein each homogenizing means is either a roll mill or a single screw refining plodder, or a dual screw refining plodder, or a refining system.

5. The process as claimed in claim 1 wherein ingredients are separated in the mixing process so that waxy materials are blended and milled first and then added to particulate and fluid materials with further mixing, milling and extrusion of the stick product.

6. A process according to claim 1 wherein the temperature does not exceed 60 degrees C.

* * * * *